United States Patent
Faler et al.

(10) Patent No.: US 10,689,314 B2
(45) Date of Patent: *Jun. 23, 2020

(54) METHODS FOR PREPARING BRIDGED BI-AROMATIC LIGANDS

(71) Applicant: Univation Technologies, LLC, Houston, TX (US)

(72) Inventors: Catherine Anne Faler, Houston, TX (US); Kevin P. Ramirez, Houston, TX (US)

(73) Assignee: Univation Technologies, LLC, Houston, TX (US)

( * ) Notice: Subject to any disclaimer, the term of this patent is extended or adjusted under 35 U.S.C. 154(b) by 182 days.

This patent is subject to a terminal disclaimer.

(21) Appl. No.: 15/568,017

(22) PCT Filed: Apr. 18, 2016

(86) PCT No.: PCT/US2016/028109
§ 371 (c)(1),
(2) Date: Oct. 20, 2017

(87) PCT Pub. No.: WO2016/172044
PCT Pub. Date: Oct. 27, 2016

(65) Prior Publication Data
US 2018/0141883 A1    May 24, 2018

Related U.S. Application Data

(60) Provisional application No. 62/150,117, filed on Apr. 20, 2015.

(51) Int. Cl.
C07C 15/14    (2006.01)
C07C 41/01    (2006.01)
C07F 5/02    (2006.01)
C07C 41/30    (2006.01)
C07F 7/00    (2006.01)
(Continued)

(52) U.S. Cl.
CPC .............. C07C 15/14 (2013.01); C07B 39/00 (2013.01); C07B 51/00 (2013.01); C07C 15/20 (2013.01); C07C 41/30 (2013.01); C07C 43/23 (2013.01); C07F 5/025 (2013.01); C07F 7/003 (2013.01);
(Continued)

(58) Field of Classification Search
None
See application file for complete search history.

(56) References Cited

U.S. PATENT DOCUMENTS

2006/0025548 A1    2/2006    Boussie et al.
2008/0269470 A1*   10/2008   Boussie ................ B01J 31/223
                                                      534/15
2011/0054122 A1    3/2011    Klosin et al.

FOREIGN PATENT DOCUMENTS

WO    2005108406    11/2005

OTHER PUBLICATIONS

International Search Report & Written Opinion for related PCT Application PCT/US2016/028109, dated Jun. 22, 2016 (11 pgs).
(Continued)

Primary Examiner — Yun Qian
(74) Attorney, Agent, or Firm — Brooks, Cameron & Huebsch, PLLC

(57) ABSTRACT

New methods for preparing bridged bi-aromatic ligands are disclosed. The methods employ aryl coupling of unprotected phenols. The ligands may be used to prepare transition metal compounds useful as catalysts in olefin polymerization.

20 Claims, 1 Drawing Sheet

(51) Int. Cl.
*C07B 39/00* (2006.01)
*C07B 51/00* (2006.01)
*C07C 15/20* (2006.01)
*C07C 43/23* (2006.01)

(52) U.S. Cl.
CPC ...... *C07C 2523/44* (2013.01); *C07C 2531/24* (2013.01); *C07C 2602/10* (2017.05)

(56) References Cited

OTHER PUBLICATIONS

Li, et al., "A Protecting-Group-Free Route to Chiral BINOL-Phosphoric Acids"; European Journal of Organic Chemistry (Jan. 1, 2011) (6 pgs).
International Preliminary Report on Patentability for related PCT Application PCT/US2016/028109, dated Nov. 2, 2017 (7 pgs).

* cited by examiner

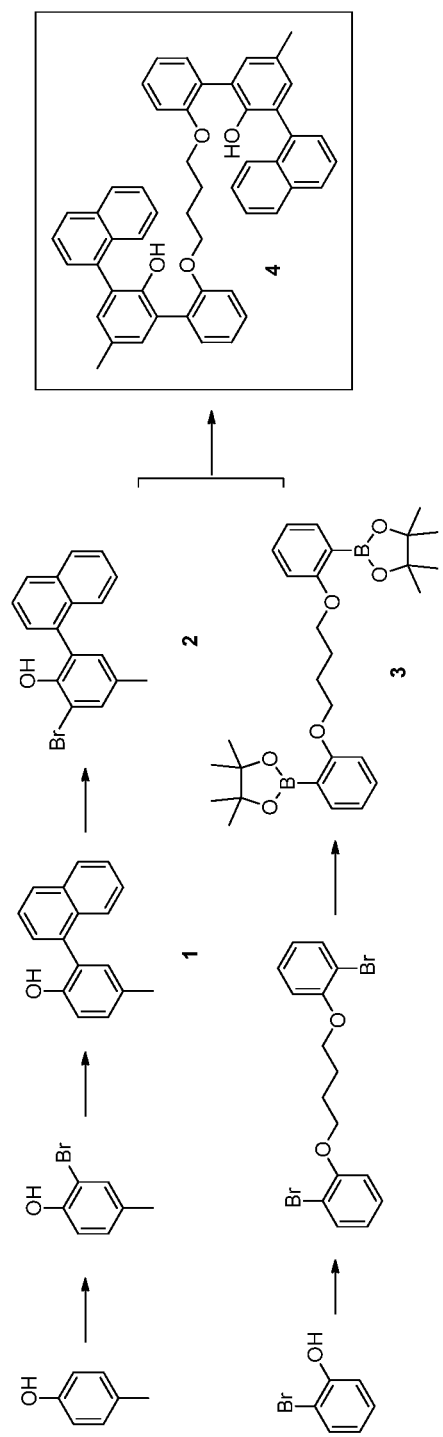

METHODS FOR PREPARING BRIDGED BI-AROMATIC LIGANDS

This application is a National Stage Application under 35 U.S.C. § 371 of International Application Number PCT/US2016/028109, filed Apr. 18, 2016 and published as WO 2016/172044 on Oct. 27, 2016, which claims the benefit to U.S. Provisional Application 62/150,117, filed Apr. 20, 2015, the entire contents of which are incorporated herein by reference in its entirety.

FIELD

The present disclosure is directed to improved methods for preparing bridged bi-aromatic ligands which are useful in the synthesis of transition metal olefin polymerization catalysts.

BACKGROUND

A major focus of the polyolefin industry in recent years has been on the development of new catalysts that deliver new and improved products. Bulky ligand transition metal compounds, for example, are now widely utilized in catalyst compositions for producing polyolefin polymers, such as polyethylene polymers.

WO 03/09162 discloses bridged bi-aromatic ligands, methods for their preparation, transition metal compounds derived therefrom and catalysts for olefin polymerization. However, the methods disclosed to synthesize the ligands involve many reaction steps and are time consuming. This increases the cost of producing the ligands and negatively impacts catalyst economics.

Therefore, it would be desirable to provide new routes to bridged bi-aromatic ligands that contain fewer steps and that are simpler to perform.

SUMMARY

In one aspect there is provided a method for preparing a bridged bi-aromatic phenol ligand of formula (I) from a compound containing at least one phenol moiety wherein the at least one phenol moiety remains unprotected during all steps of the method and the method comprises one or more steps of aryl coupling;

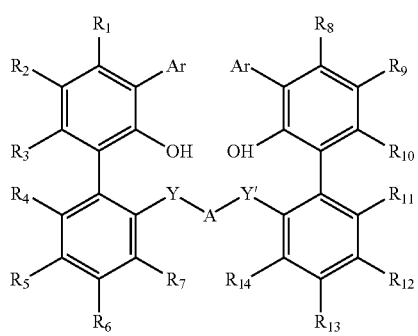

(I)

wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ is independently selected from the group consisting of hydride, halide, optionally substituted hydrocarbyl, heteroatom-containing optionally substituted hydrocarbyl, alkoxy, aryloxy, silyl, boryl, dialkyl amino, alkylthio, arylthio and seleno; optionally two or more R groups can combine together into ring structures with such ring structures having from 3 to 100 non-hydrogen atoms in the ring; A is a bridging group having from one to 50 non-hydrogen atoms; Y and Y' are independently selected from O, S, $NR^a$ and $PR^a$ wherein $R^a$ is optionally substituted hydrocarbyl; Ar is optionally substituted aryl or optionally substituted heteroaryl.

The method may comprise at least one step of Negishi coupling. The method may comprise at least one step of Suzuki coupling. The method may comprise both at least one step of Negishi coupling and at least one step of Suzuki coupling.

The method may comprise the step of:
treating a unprotected phenol of formula (II) with a compound of formula (III)

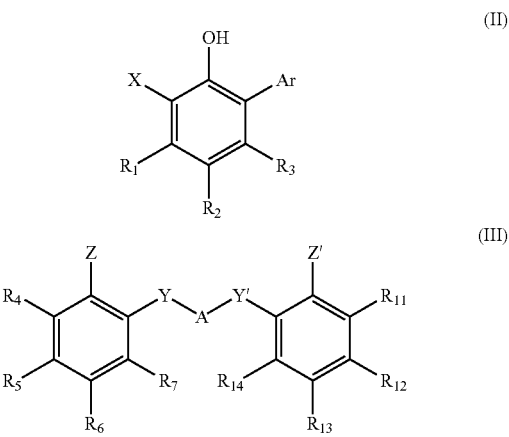

in the presence of a catalyst so as to form the compound of formula (I); wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ is independently selected from the group consisting of hydride, halide, optionally substituted hydrocarbyl, heteroatom-containing optionally substituted hydrocarbyl, alkoxy, aryloxy, silyl, boryl, dialkyl amino, alkylthio, arylthio and seleno; optionally two or more R groups can combine together into ring structures with such ring structures having from 3 to 100 non-hydrogen atoms in the ring; A is a bridging group having from one to 50 non-hydrogen atoms; Y and Y' are independently selected from O, S, $NR^a$ and $PR^a$ wherein $R^a$ is optionally substituted hydrocarbyl; X is halide; Ar is optionally substituted aryl or optionally substituted heteroaryl; Z and Z' are independently selected from $BR^b_2$ and $BF_3^-M^+$, wherein $R^b$ is independently selected from hydride, alkyl, hydroxy and alkoxy, wherein when both of $R^b$ are alkoxy, optionally they may combine to form a ring structure of formula $BO_2R^b_2$, and wherein $M^+$ is an alkali metal cation.

The compound of formula (II) may be prepared by treating a compound of formula (IV) with a compound of formula (V);

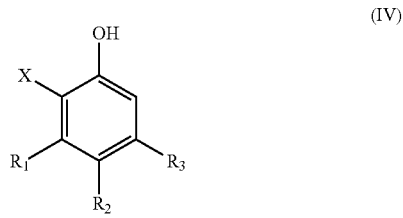

$ArBR^b{}_2$ or $ArBF_3^-M^+$ (V)

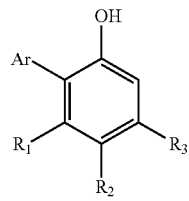

(VI)

in the presence of a catalyst so as to yield a compound of formula (VI); and further treating the compound of formula (VI) with a source of halogen so as to yield the compound of formula (II); wherein X is halide; $R^1$, $R^2$, $R^3$, Ar, $BR^b{}_2$ and $M^+$ are as hereinbefore defined.

The compound of formula (II) may be prepared by halogenating a compound of formula (VII) to yield a compound of formula (VIII);

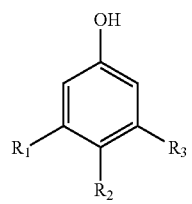

(VII)

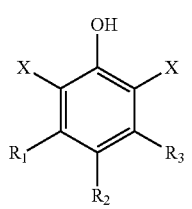

(VIII)

and further treating the compound of formula (VIII) with a compound of formula (V) in the presence of a catalyst.

The method may comprise the steps of:
a) treating a compound of formula (IV) with a compound of formula (V) in the presence of a catalyst so as to yield a compound of formula (VI);

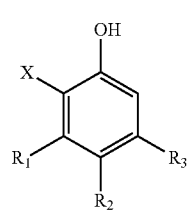

(IV)

$ArBR^b{}_2$ or $ArBF_3^-M^+$ (V)

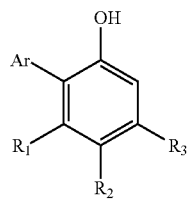

(VI)

b) treating the compound of formula (VI) with a source of halogen so as to yield the compound of formula (II); and c) treating the unprotected phenol of formula (II) with a compound of formula (III) to yield the compound of formula (I);

wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, and $R^{14}$ is independently selected from the group consisting of hydride, halide, optionally substituted hydrocarbyl, heteroatom-containing optionally substituted hydrocarbyl, alkoxy, aryloxy, silyl, boryl, dialkyl amino, alkylthio, arylthio and seleno; optionally two or more R groups can combine together into ring structures with such ring structures having from 3 to 100 non-hydrogen atoms in the ring; A is a bridging group having from one to 50 non-hydrogen atoms; Y and Y' are independently selected from O, S, $NR^a$ and $PR^a$ wherein $R^a$ is optionally substituted hydrocarbyl; X is halide; Ar is optionally substituted aryl or optionally substituted heteroaryl; Z and Z' are independently selected from $BR^b{}_2$ and $BF_3^-M^+$, wherein $R^b$ is independently selected from hydride, alkyl, hydroxy and alkoxy, wherein when both of $R^b$ are alkoxy, optionally they may combine to form a ring structure of formula $BO_2R^b{}_2$, and wherein $M^+$ is an alkali metal cation.

In any one of the hereinbefore disclosed embodiments each of $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ may be independently selected from the group consisting of hydride, halide, optionally substituted alkyl, heteroalkyl, aryl, heteroaryl, alkoxyl, aryloxyl, silyl, dialkylamino, alkylthio and arylthio.

In any one of the hereinbefore disclosed embodiments each of $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ may be independently selected from the group consisting of hydride, and optionally substituted alkyl and aryl.

In any one of the hereinbefore disclosed embodiments the bridging group A may be selected from the group consisting of optionally substituted divalent hydrocarbyl and divalent heteroatom containing hydrocarbyl.

In any one of the hereinbefore disclosed embodiments the bridging group A may be selected from the group consisting of optionally substituted divalent alkyl, alkenyl, alkynyl, heteroalkyl, heteroalkenyl, heteroalkynyl, carbocycle, heterocarbocycle, aryl, heteroaryl and silyl.

In any one of the hereinbefore disclosed embodiments the bridging group A may be an optionally substituted divalent alkyl.

In any one of the hereinbefore disclosed embodiments the bridging group A may be represented by the general formula $-(QR^{15}{}_{2-z''})_{z'}-$ wherein each Q is either carbon or silicon and each $R^{15}$ may be the same or different from the others such that each $R^{15}$ is selected from the group consisting of hydride and optionally substituted hydrocarbyl and heteroatom containing hydrocarbyl, and optionally two or more $R^{15}$ groups may be joined into a ring structure having from 3 to 50 atoms in the ring structure not counting hydrogen atoms; z' is an integer from 1 to 10; and z" is 0, 1 or 2.

In any one of the hereinbefore disclosed embodiments Ar may be optionally substituted phenyl, naphthyl, biphenyl, anthracenyl, and phenanthrenyl.

In any one of the hereinbefore disclosed embodiments Ar may be thiophene, pyridine, isoxazole, pyrazole, pyrrole, furan or benzo-fused analogues of these rings.

A major advantage of the herein disclosed methods is that the number of reaction steps may be reduced relative to known methods for producing bridged bi-aromatic ligands.

A further advantage of the herein disclosed methods is that, in contrast to previously disclosed methods which employ protection chemistry, protection and deprotection of a phenol is not necessary.

In any one of the hereinbefore disclosed embodiments the catalyst may comprise a nickel or palladium catalyst.

In any one of the hereinbefore disclosed embodiments the palladium catalyst may comprise a palladium phosphine catalyst. The palladium catalyst may comprise, for example, bis(tri-tert-butylphosphine)palladium, tetrakis(triphenylphosphine)palladium(0) (Pd(PPh$_3$)$_4$), bis[1,2-bis(diphenylphosphino)ethane]palladium(0) (Pd(dppe)$_2$), 1,1'-bis(diphenylphosphino)ferrocene palladium (Pd(dppf)), (2,2'-bis(diphenylphosphino)-1,1'-binaphthyl palladium (Pd (BINAP).

The palladium phosphine catalyst may comprise palladium tetrakis(triphenylphosphine).

In any one of the hereinbefore disclosed embodiments the catalyst may further comprise a base.

In any one of the hereinbefore disclosed embodiments the base may comprise an alkali metal carbonate, alkali metal phosphate, alkali metal hydroxide, alkali metal alkoxide or an amine.

In any one of the hereinbefore disclosed embodiments X may be bromo or chloro. The source of halogen may be bromine or chlorine.

In any one of the hereinbefore disclosed embodiments the compound of formula ArBR$^b{}_2$ or ArBF$_3{}^-$M$^+$ may be selected from an optionally substituted arylborane, heteroarylborane, aryl boronic acid, heteroaryl boronic acid, aryl boronic ester, heteroaryl boronic ester, aryl trifluoroborate metal salt or heteroaryl trifluoroborate metal salt.

In any one of the hereinbefore disclosed embodiments the ligand of formula (I) may have formula (IX);

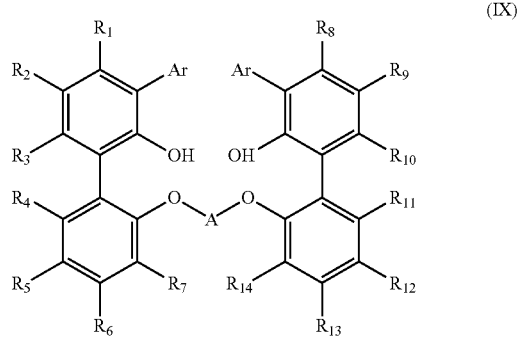

(IX)

wherein R$^1$, R$^2$, R$^3$, R$^4$, R$^5$, R$^6$, R$^7$, R$^8$, R$^9$, R$^{10}$, R$^{11}$, R$^{12}$, R$^{13}$ and R$^{14}$ Ar and A are as hereinbefore defined.

In another aspect there is provided a ligand of formula (I) or formula (IX) prepared by any one of the hereinbefore disclosed methods.

BRIEF DESCRIPTION OF THE DRAWINGS

FIG. 1 depicts an exemplary reaction scheme in accordance with this disclosure.

DETAILED DESCRIPTION

Before the present compounds, components, compositions, and/or methods are disclosed and described, it is to be understood that unless otherwise indicated this invention is not limited to specific compounds, components, compositions, reactants, reaction conditions, ligands, transition metal compounds, or the like, as such may vary, unless otherwise specified. It is also to be understood that the terminology used herein is for the purpose of describing particular embodiments only and is not intended to be limiting.

It must also be noted that, as used in the specification and the appended claims, the singular forms "a," "an" and "the" include plural referents unless otherwise specified. Thus, for example, reference to "a halogen atom" as in a moiety "substituted with a halogen atom" includes more than one halogen atom, such that the moiety may be substituted with two or more halogen atoms, reference to "a substituent" includes one or more substituents, reference to "a ligand" includes one or more ligands, and the like.

As used herein, all reference to the Periodic Table of the Elements and groups thereof is to the NEW NOTATION published in HAWLEY'S CONDENSED CHEMICAL DICTIONARY, Thirteenth Edition, John Wiley & Sons, Inc., (1997) (reproduced there with permission from IUPAC), unless reference is made to the Previous IUPAC form noted with Roman numerals (also appearing in the same), or unless otherwise noted.

Disclosed herein are methods for preparing bridged bi-aromatic ligands which are advantageous in comparison to known preparation methods. The disclosed methods do not require the use of protecting group chemistry which greatly reduces the number of reaction steps. The ligands find use in the preparation of transition metal compounds useful as catalysts in olefin polymerization.

General Definitions

The term "independently selected" is used herein to indicate that the R groups, e.g., R$^1$, R$^2$, R$^3$, R$^4$, and R$^5$ can be identical or different (e.g. R$^1$, R$^2$, R$^3$, R$^4$, and R$^5$ may all be substituted alkyls or R$^1$ and R$^2$ may be a substituted alkyl and R$^3$ may be an aryl, etc.). Use of the singular includes use of the plural and vice versa (e.g., a hexane solvent, includes hexanes). A named R group will generally have the structure that is recognized in the art as corresponding to R groups having that name. The terms "compound" and "complex" are generally used interchangeably in this specification, but those of skill in the art may recognize certain compounds as complexes and vice versa. For the purposes of illustration, representative certain groups are defined herein. These definitions are intended to supplement and illustrate, not preclude, the definitions known to those of skill in the art.

"Optional" or "optionally" means that the subsequently described event or circumstance may or may not occur, and that the description includes instances where said event or circumstance occurs and instances where it does not. For example, the phrase "optionally substituted hydrocarbyl" means that a hydrocarbyl moiety may or may not be substituted and that the description includes both unsubstituted hydrocarbyl and hydrocarbyl where there is substitution.

The term "alkyl" as used herein refers to a branched or unbranched saturated hydrocarbon group typically although not necessarily containing 1 to about 50 carbon atoms, such as methyl, ethyl, n-propyl, isopropyl, n-butyl, iso-butyl, t-butyl, octyl, decyl, and the like, as well as cycloalkyl groups such as cyclopentyl, cyclohexyl and the like. Generally, although again not necessarily, alkyl groups herein may contain 1 to about 12 carbon atoms. The term "lower alkyl" intends an alkyl group of one to six carbon atoms, specifically one to four carbon atoms. "Substituted alkyl" refers to alkyl substituted with one or more substituent groups (e.g., benzyl or chloromethyl), and the terms "heteroatom-containing alkyl" and "heteroalkyl" refer to alkyl in which at least one carbon atom is replaced with a heteroatom (e.g., —$CH_2OCH_3$ is an example of a heteroalkyl).

The term "alkenyl" as used herein refers to a branched or unbranched hydrocarbon group typically although not necessarily containing 2 to about 50 carbon atoms and at least one double bond, such as ethenyl, n-propenyl, iso-propenyl, n-butenyl, iso-butenyl, octenyl, decenyl, and the like. Generally, although again not necessarily, alkenyl groups herein contain 2 to about 12 carbon atoms. The term "lower alkenyl" refers to an alkenyl group of two to six carbon atoms, specifically two to four carbon atoms. "Substituted alkenyl" refers to alkenyl substituted with one or more substituent groups, and the terms "heteroatom-containing alkenyl" and "heteroalkenyl" refer to alkenyl in which at least one carbon atom is replaced with a heteroatom.

The term "alkynyl" as used herein refers to a branched or unbranched hydrocarbon group typically although not necessarily containing 2 to about 50 carbon atoms and at least one triple bond, such as ethynyl, n-propynyl, iso-propynyl, n-butynyl, isobutynyl, octynyl, decynyl, and the like. Generally, although again not necessarily, alkynyl groups herein may have 2 to about 12 carbon atoms. The term "lower alkynyl" refers to an alkynyl group of two to six carbon atoms, specifically three or four carbon atoms. "Substituted alkynyl" refers to alkynyl substituted with one or more substituent groups, and the terms "heteroatom-containing alkynyl" and "heteroalkynyl" refer to alkynyl in which at least one carbon atom is replaced with a heteroatom.

The term "alkoxy" as used herein intends an alkyl group bound through a single, terminal ether linkage; that is, an "alkoxy" group may be represented as —O-alkyl where alkyl is as defined above. A "lower alkoxy" group refers to an alkoxy group having one to six, more specifically one to four, carbon atoms. The term "aryloxy" is used in a similar fashion, with aryl as defined below. The term "hydroxy" refers to —OH.

Similarly, the term "alkylthio" as used herein intends an alkyl group bound through a single, terminal thioether linkage; that is, an "alkylthio" group may be represented as —S-alkyl where alkyl is as defined above. A "lower alkyl thio" group refers to an alkyl thio group having one to six, more specifically one to four, carbon atoms. The term "arylthio" is used similarly, with aryl as defined below. The term "thioxy" refers to —SH.

The term "allenyl" is used herein in the conventional sense to refer to a molecular segment having the structure —CH=C=$CH_2$. An "allenyl" group may be unsubstituted or substituted with one or more non-hydrogen substituents.

The term "aryl" as used herein, and unless otherwise specified, refers to an aromatic substituent containing a single aromatic ring or multiple aromatic rings that are fused together, linked covalently, or linked to a common group such as a methylene or ethylene moiety. More specific aryl groups contain one aromatic ring or two or three fused or linked aromatic rings, e.g., phenyl, naphthyl, biphenyl, anthracenyl, phenanthrenyl, and the like. The aryl substituents may have 1 to about 200 carbon atoms, typically 1 to about 50 carbon atoms, and specifically 1 to about 20 carbon atoms. "Substituted aryl" refers to an aryl moiety substituted with one or more substituent groups, (e.g., tolyl, mesityl and perfluorophenyl) and the terms "heteroatom-containing aryl" and "heteroaryl" refer to aryl in which at least one carbon atom is replaced with a heteroatom (e.g., rings such as thiophene, pyridine, isoxazole, pyrazole, pyrrole, furan, etc. or benzo-fused analogues of these rings are included in the term "heteroaryl"). In some embodiments herein, multi-ring moieties are substituents and in such an embodiment the multi-ring moiety can be attached at an appropriate atom. For example, "naphthyl" can be 1-naphthyl or 2-naphthyl; "anthracenyl" can be 1-anthracenyl, 2-anthracenyl or 9-anthracenyl; and "phenanthrenyl" can be 1-phenanthrenyl, 2-phenanthrenyl, 3-phenanthrenyl, 4-phenanthrenyl or 9-phenanthrenyl.

The term "aralkyl" refers to an alkyl group with an aryl substituent, and the term "aralkylene" refers to an alkylene group with an aryl substituent; the term "alkaryl" refers to an aryl group that has an alkyl substituent, and the term "alkarylene" refers to an arylene group with an alkyl substituent.

The terms "halo" and "halogen" are used in the conventional sense to refer to a chloro, bromo, fluoro or iodo substituent. The terms "haloalkyl," "haloalkenyl" or "haloalkynyl" (or "halogenated alkyl," "halogenated alkenyl," or "halogenated alkynyl") refers to an alkyl, alkenyl or alkynyl group, respectively, in which at least one of the hydrogen atoms in the group has been replaced with a halogen atom.

The term "heteroatom-containing" as in a "heteroatom-containing hydrocarbyl group" refers to a molecule or molecular fragment in which one or more carbon atoms is replaced with an atom other than carbon, e.g., nitrogen, oxygen, sulfur, phosphorus, boron or silicon. Similarly, the term "heteroalkyl" refers to an alkyl substituent that is heteroatom-containing, the term "heterocyclic" refers to a cyclic substituent that is heteroatom-containing, the term "heteroaryl" refers to an aryl substituent that is heteroatom-containing, and the like. When the term "heteroatom-containing" appears prior to a list of possible heteroatom-containing groups, it is intended that the term apply to every member of that group. That is, the phrase "heteroatom-containing alkyl, alkenyl and alkynyl" is to be interpreted as "heteroatom-containing alkyl, heteroatom-containing alkenyl and heteroatom-containing alkynyl."

"Hydrocarbyl" refers to hydrocarbyl radicals containing 1 to about 50 carbon atoms, specifically 1 to about 24 carbon atoms, most specifically 1 to about 16 carbon atoms, including branched or unbranched, saturated or unsaturated species, such as alkyl groups, alkenyl groups, aryl groups, and the like. The term "lower hydrocarbyl" refers to a hydrocarbyl group of one to six carbon atoms, specifically one to four carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom.

By "substituted" as in "substituted hydrocarbyl," "substituted aryl," "substituted alkyl," "substituted alkenyl" and the like, as alluded to in some of the aforementioned definitions, is meant that in the hydrocarbyl, hydrocarbylene, alkyl, alkenyl, aryl or other moiety, at least one hydrogen atom bound to a carbon atom is replaced with one or more substituents that are functional groups such as hydroxyl, alkoxy, alkylthio, phosphino, amino, halo, silyl, and the like. When the term "substituted" appears prior to a list of possible substituted groups, it is intended that the term apply to every member of that group. That is, the phrase "substituted alkyl, alkenyl and alkynyl" is to be interpreted as "substituted alkyl, substituted alkenyl and substituted alkynyl." Similarly, "optionally substituted alkyl, alkenyl and alkynyl" is to be interpreted as "optionally substituted alkyl, optionally substituted alkenyl and optionally substituted alkynyl."

By "divalent" as in "divalent hydrocarbyl", "divalent alkyl", "divalent aryl" and the like, is meant that the hydrocarbyl, alkyl, aryl or other moiety is bonded at two points to atoms, molecules or moieties with the two bonding points being covalent bonds. The term "aromatic" is used in its usual sense, including unsaturation that is essentially delocalized across multiple bonds, such as around a ring.'

As used herein the term "silyl" refers to the $-SiZ^1Z^2Z^3$ radical, where each of $Z^1$, $Z^2$, and $Z^3$ is independently selected from the group consisting of hydride and optionally substituted alkyl, alkenyl, alkynyl, heteroatom-containing alkyl, heteroatom-containing alkenyl, heteroatom-containing alkynyl, aryl, heteroaryl, alkoxy, aryloxy, amino, silyl and combinations thereof.

As used herein the term "boryl" refers to the $-BZ^1Z^2$ group, where each of $Z^1$ and $Z^2$ is as defined above.

As used herein, the term "phosphino" refers to the group $PZ^1Z^2$, where each of and $Z^2$ is as defined above. As used herein, the term "phosphine" refers to the group $PZ^1Z^2Z^3$, where each of $Z^1$, $Z^2$ and $Z^3$ is as defined above. The term "amino" is used herein to refer to the group $-NZ^1Z^2$, where each of $Z^1$ and $Z^2$ is as defined above. The term "amine" is used herein to refer to the group $NZ^1Z^2Z^3$, where each of $Z^1$, $Z^2$ and $Z^3$ is as defined above.

The term "saturated" refers to lack of double and triple bonds between atoms of a radical group such as ethyl, cyclohexyl, pyrrolidinyl, and the like. The term "unsaturated" refers to the presence of one or more double and triple bonds between atoms of a radical group such as vinyl, acetylide, oxazolinyl, cyclohexenyl, acetyl and the like.

Other abbreviations used herein include: "iPr" to refer to isopropyl; "tBu" to refer to tertbutyl; "Me" to refer to methyl; "Et" to refer to ethyl; and "Ph" refers to phenyl.

The ligands of the present disclosure may have formula (IX):

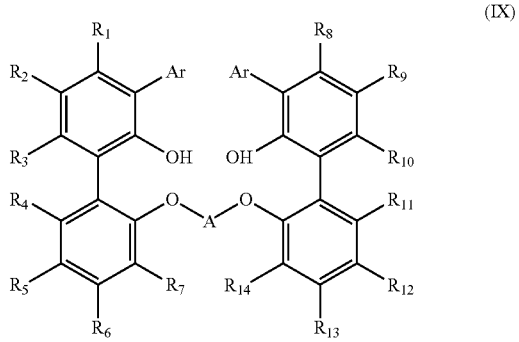

wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, and $R^{14}$ is independently selected from the group consisting of hydride, halide, optionally substituted hydrocarbyl, heteroatom-containing optionally substituted hydrocarbyl, alkoxy, aryloxy, silyl, boryl, dialkyl amino, alkylthio, arylthio and seleno; optionally two or more R groups can combine together into ring structures with such ring structures having from 3 to 100 non-hydrogen atoms in the ring; A is a bridging group having from one to 50 non-hydrogen atoms; Ar is optionally substituted aryl or optionally substituted heteroaryl.

Each of $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ may be independently selected from the group consisting of hydride, halide, optionally substituted hydrocarbyl, and heteroatom-containing optionally substituted hydrocarbyl; A is a divalent alkyl; Ar is optionally substituted aryl or optionally substituted heteroaryl.

Each of $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ may be independently selected from the group consisting of hydride and optionally substituted hydrocarbyl; A is a divalent alkyl; Ar is optionally substituted phenyl, naphthyl, biphenyl, anthracenyl, phenanthrenyl, thiophene, pyridine, isoxazole, pyrazole, pyrrole, furan or benzo-fused analogues of these rings.

Specific ligands which may be prepared by the methods disclosed herein include:

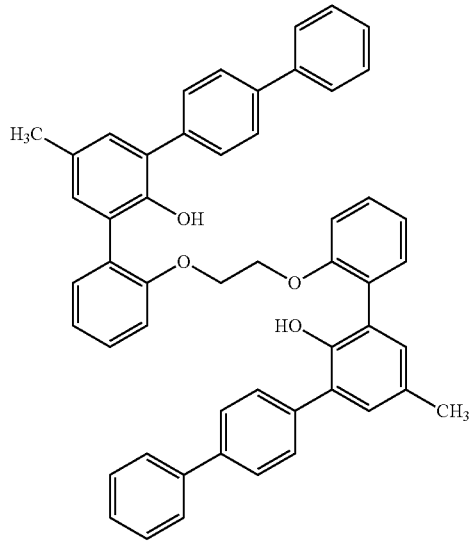

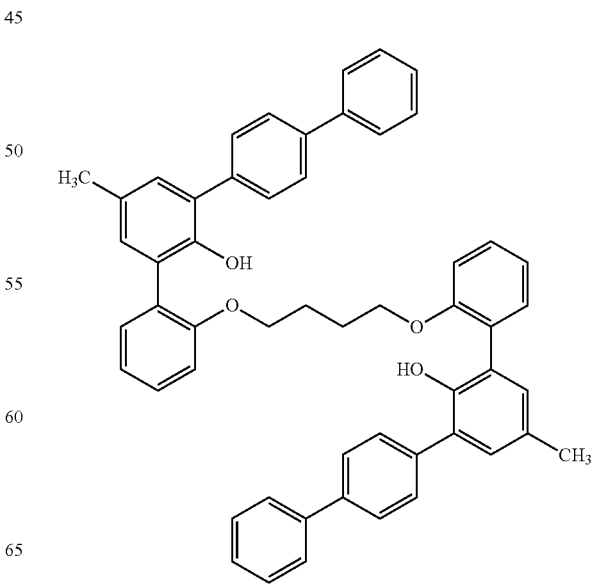

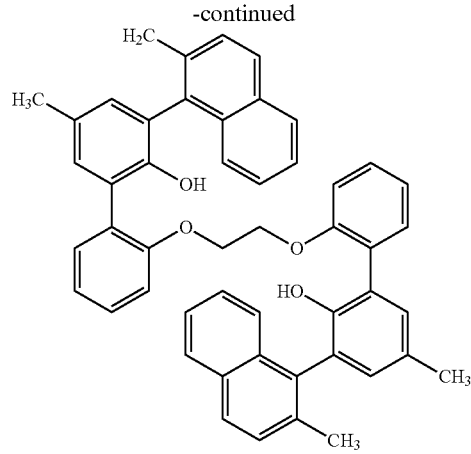
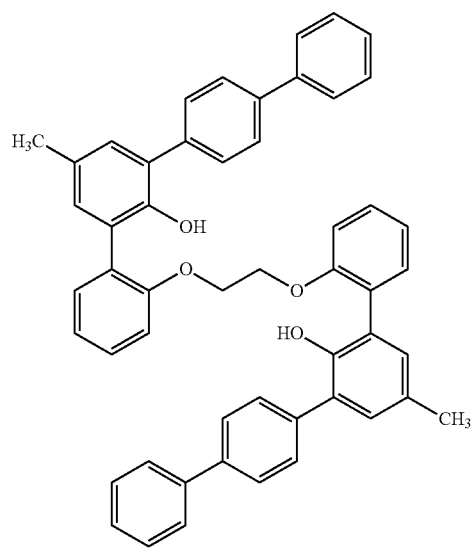
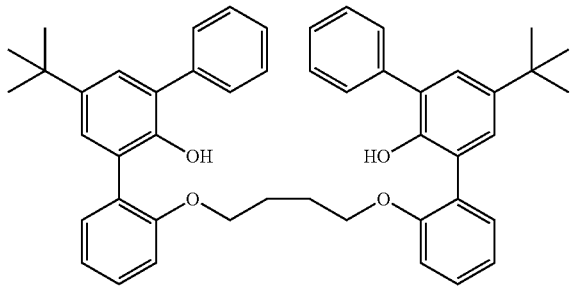
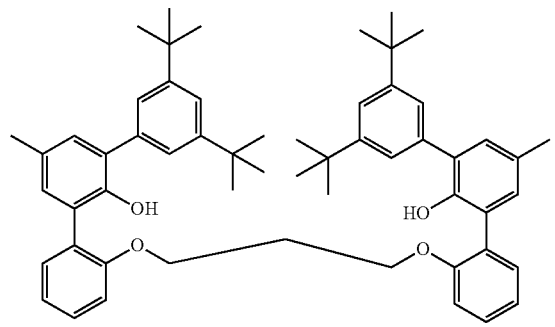
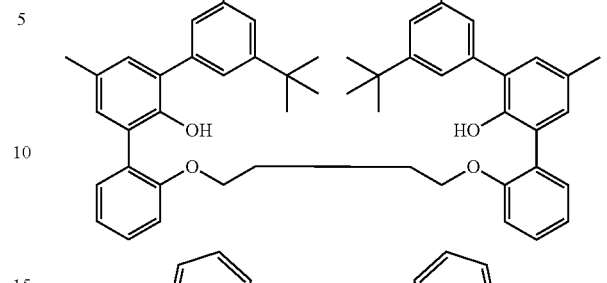
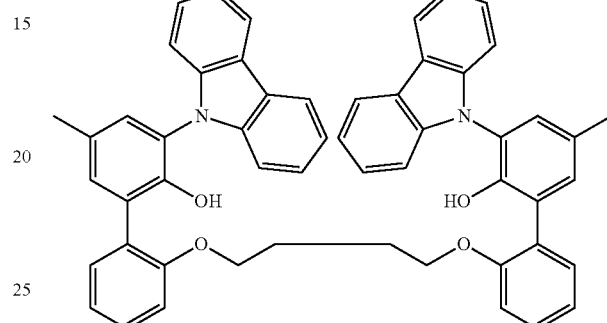
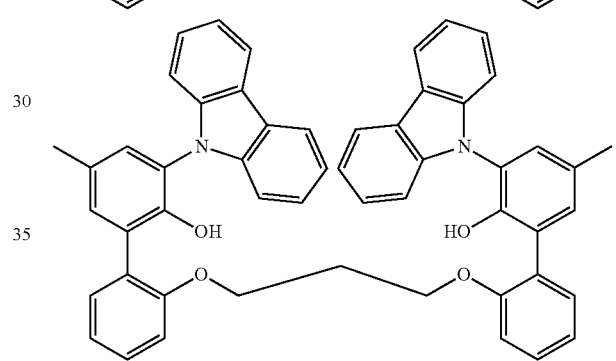
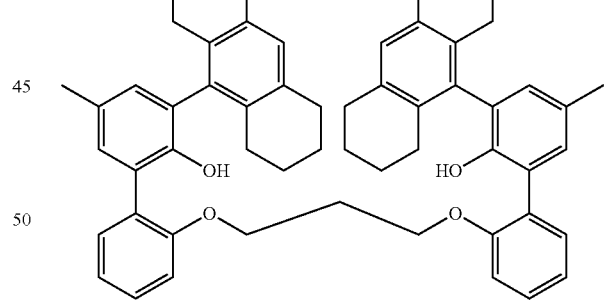
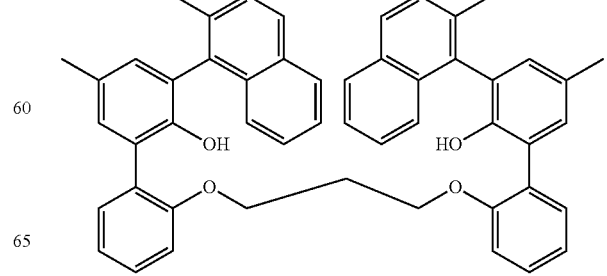

13
-continued
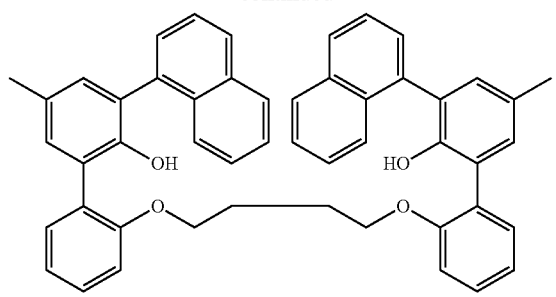
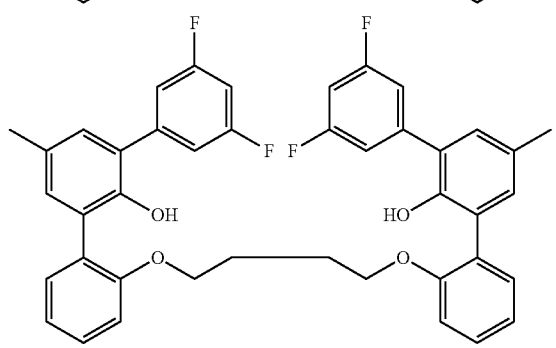
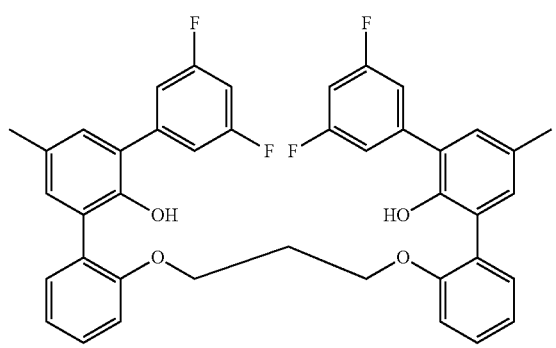
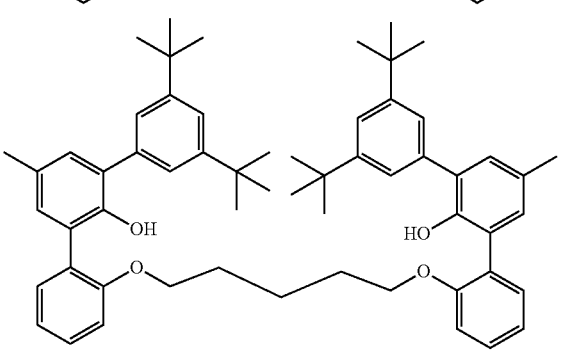
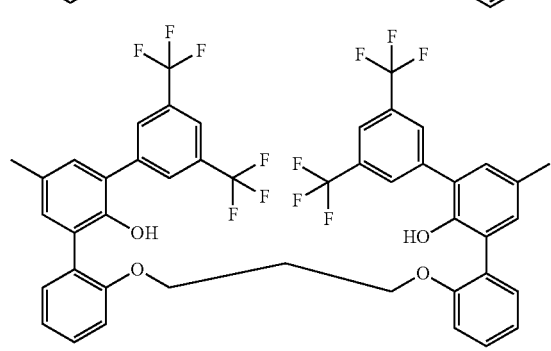
14
-continued
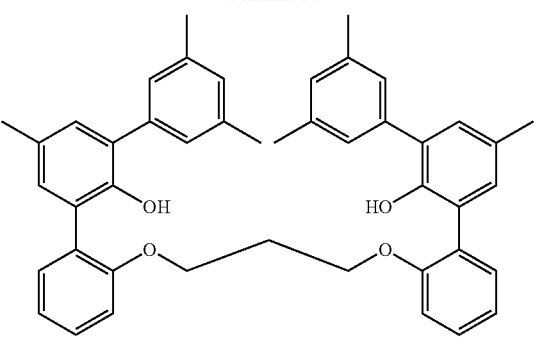
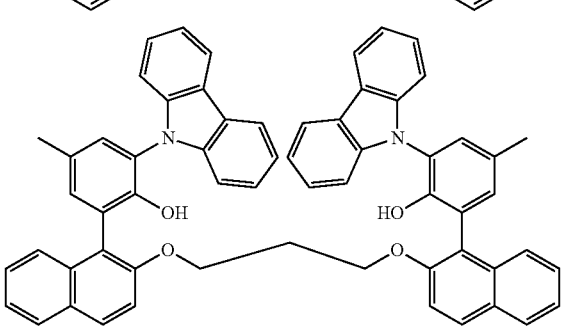
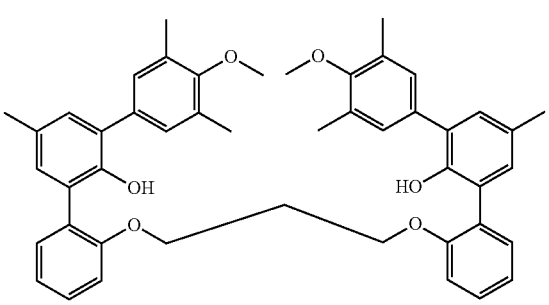
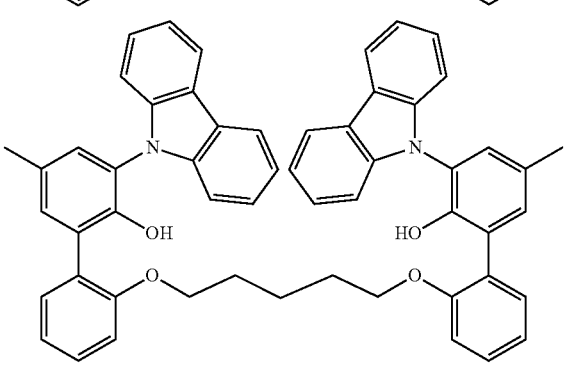
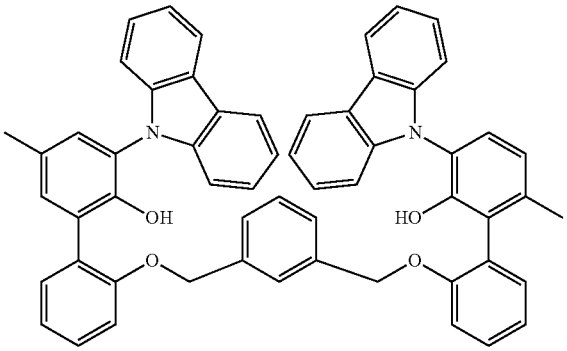

-continued
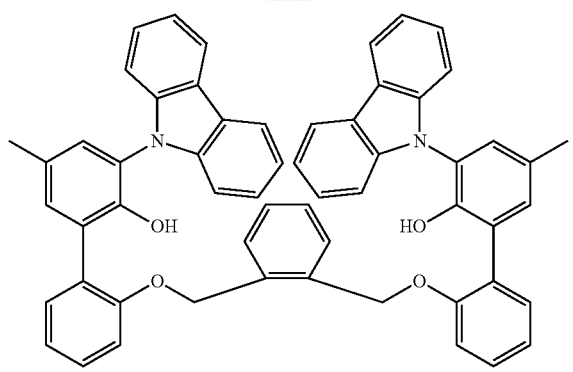
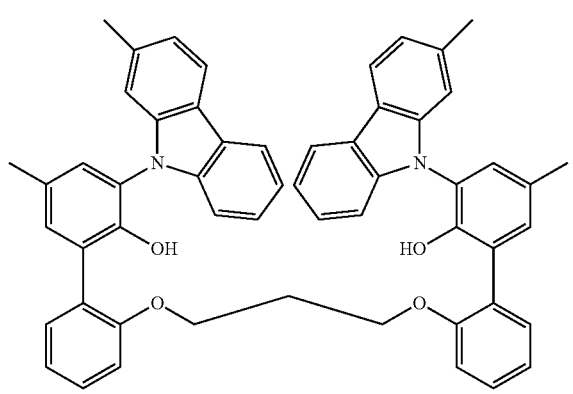
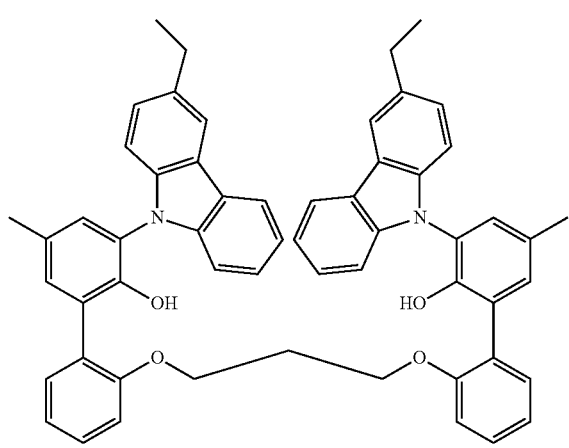
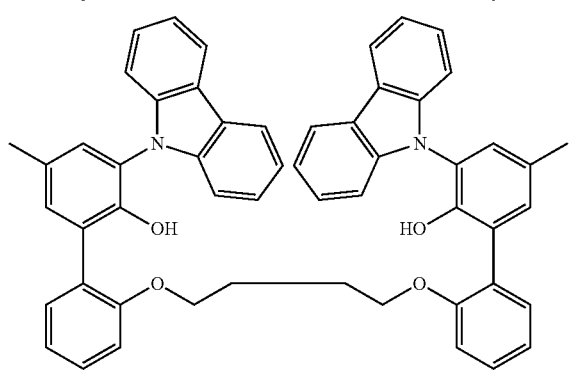
-continued
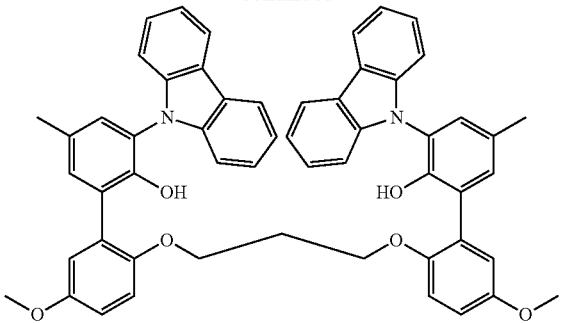
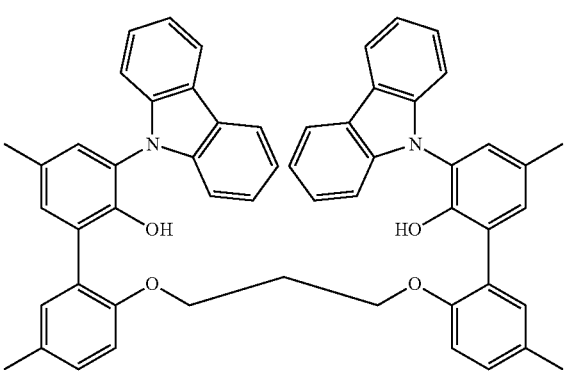
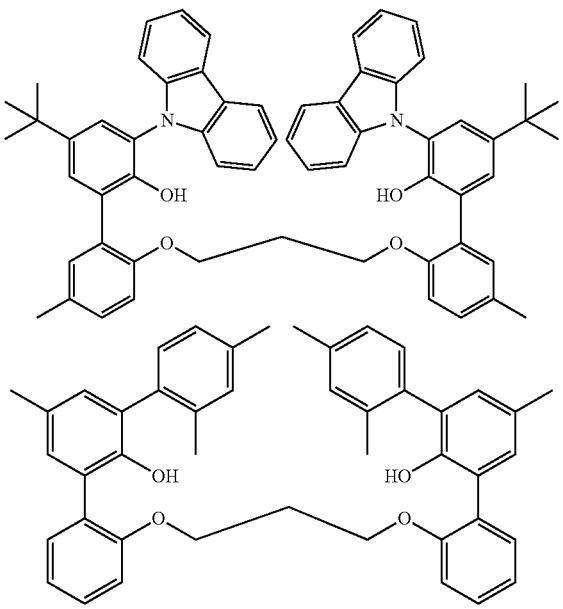
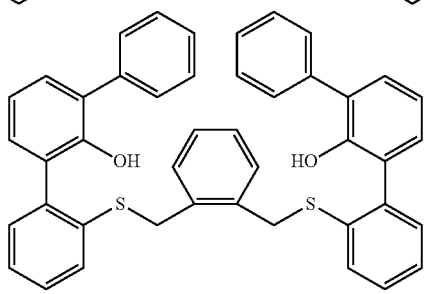

-continued
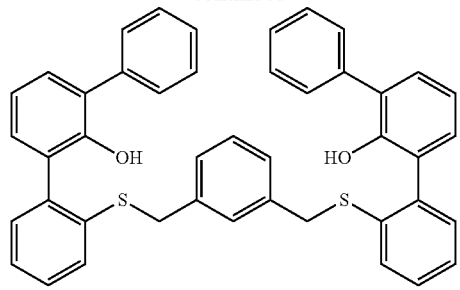
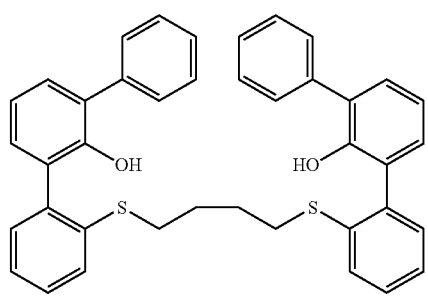
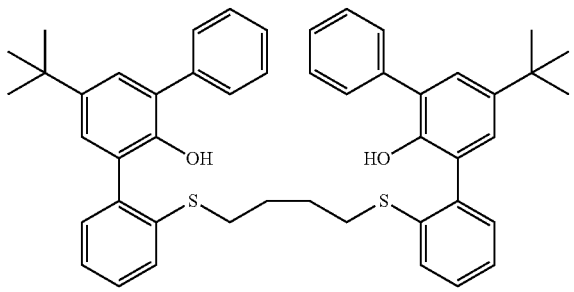
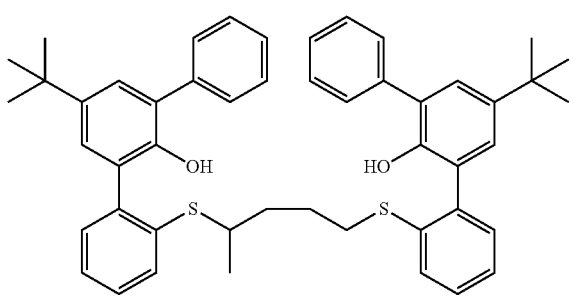
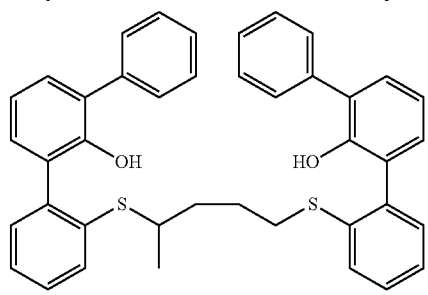
-continued
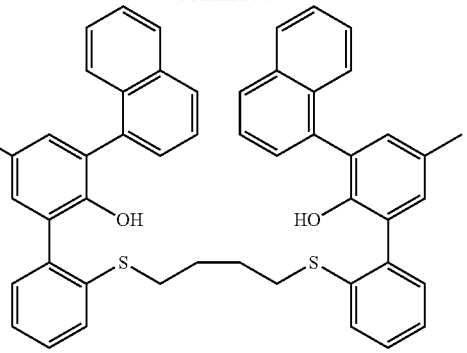
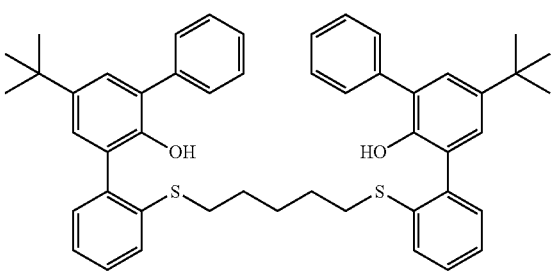
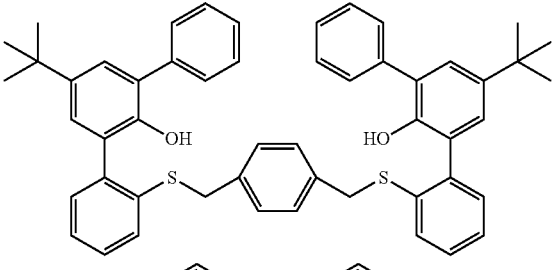
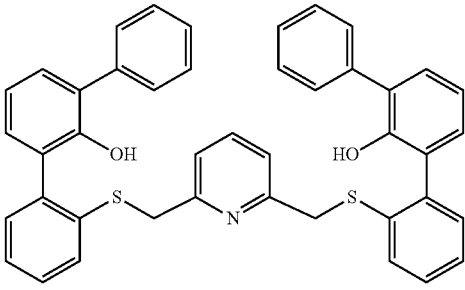
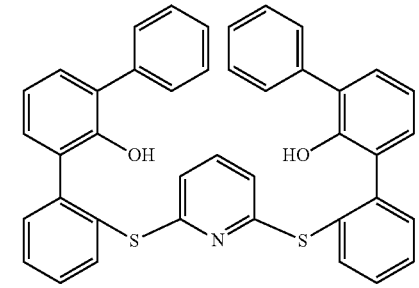
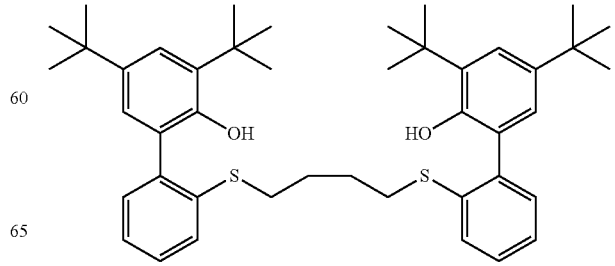

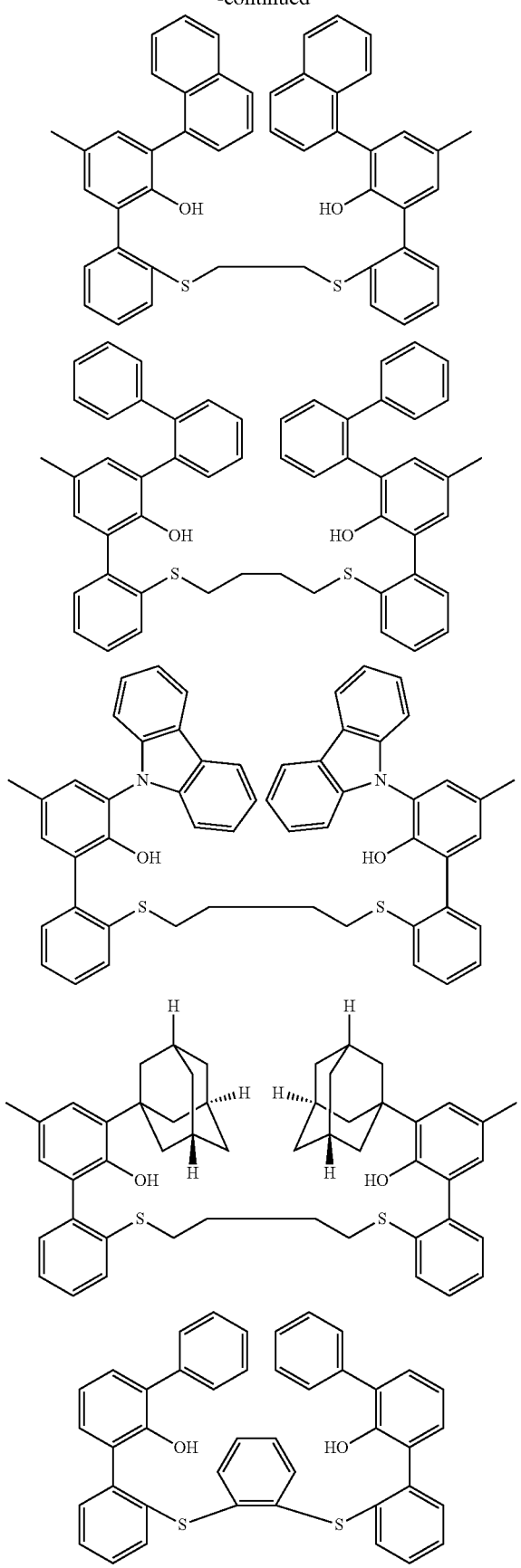
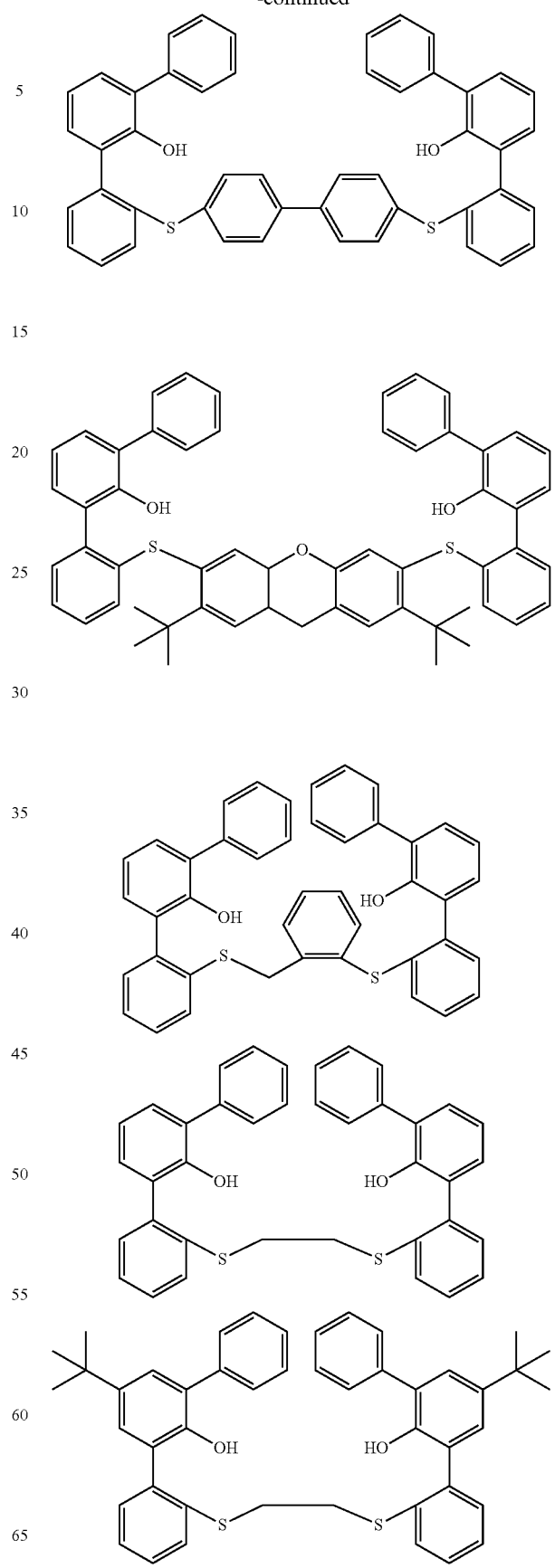

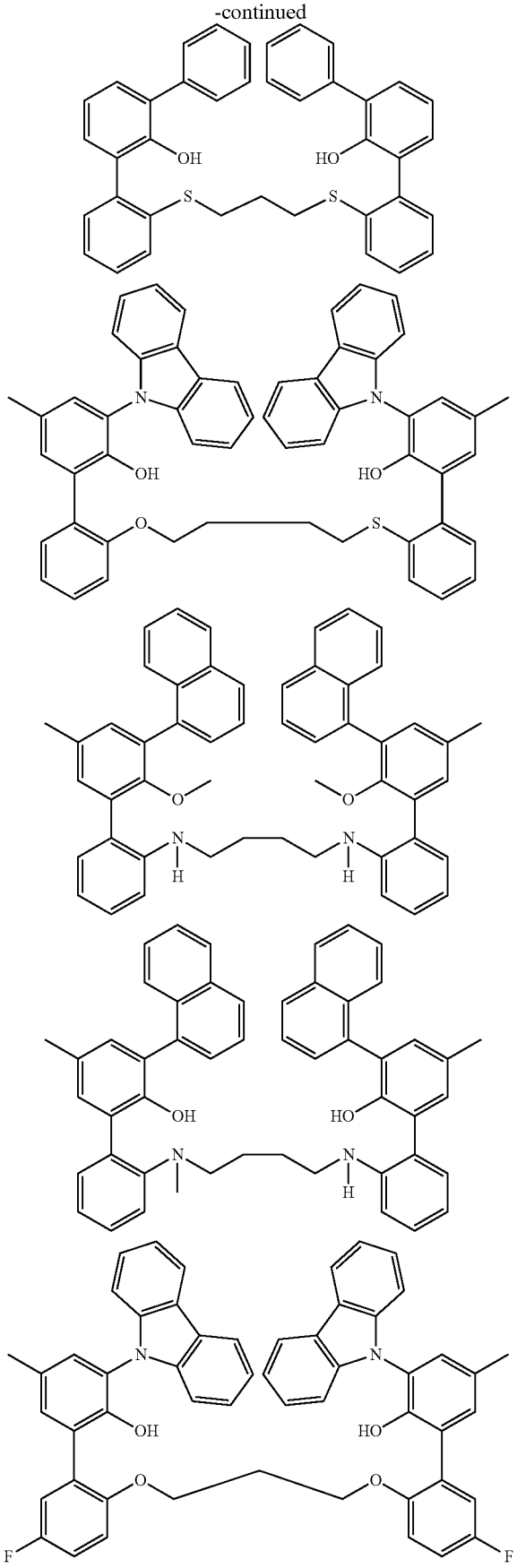
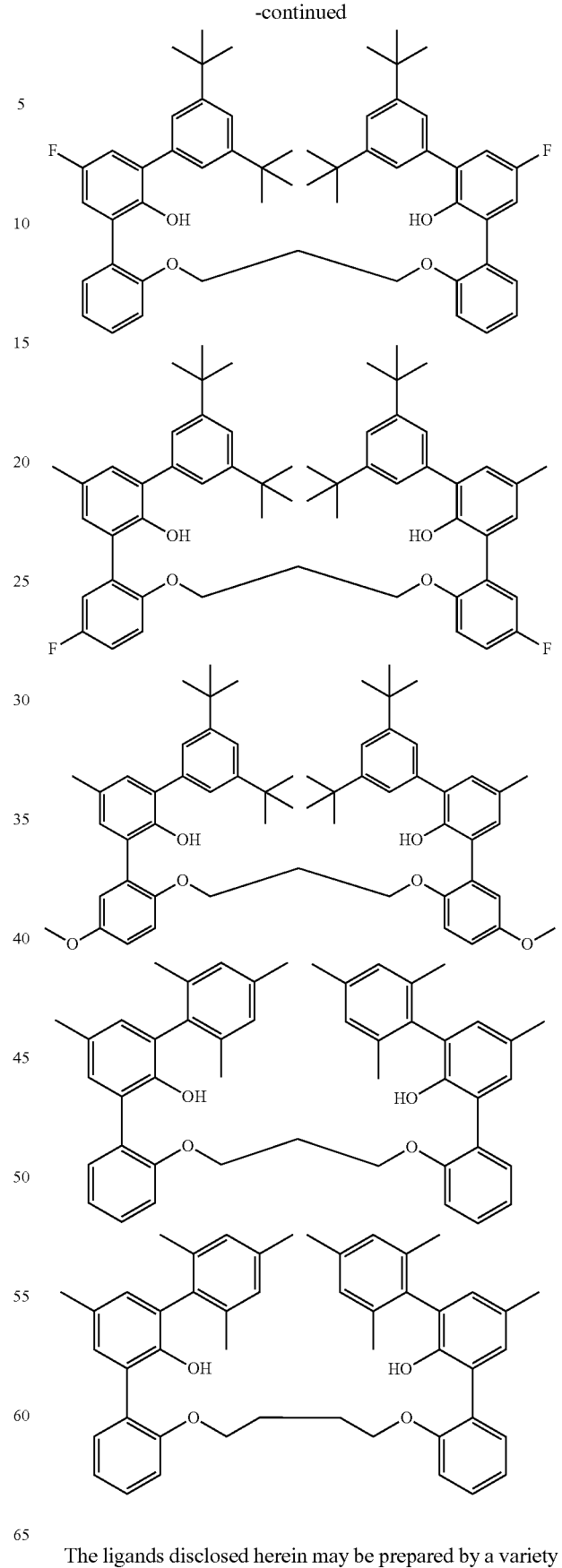
The ligands disclosed herein may be prepared by a variety of methods. In general the ligands may be prepared by employing aryl coupling of unprotected phenols. The aryl coupling may be Suzuki coupling or Negishi coupling or both.

The following schemes illustrate general methods for the preparation of the ligands.

In Scheme 1, a phenol is halogenated and the resulting product subjected to Suzuki coupling followed by further halogenation.

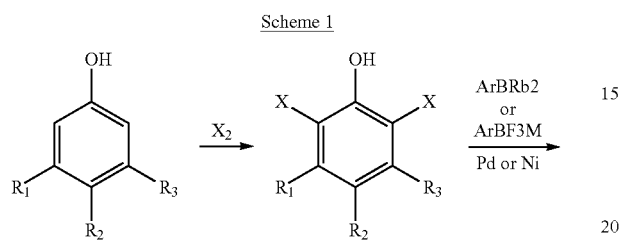

Scheme 1

In Scheme 2 an alternate route to an arylated halophenol is illustrated.

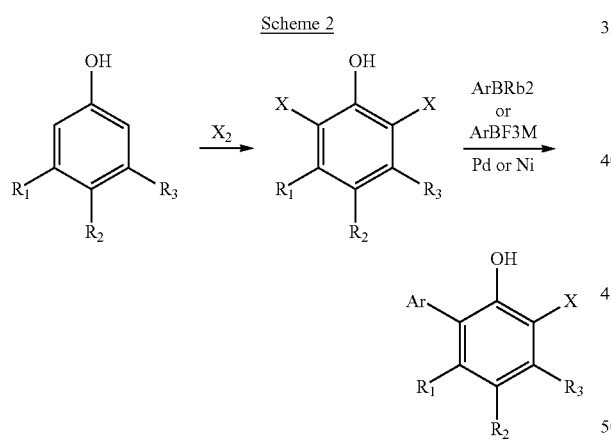

Scheme 2

In Scheme 3, a halogenated phenol is reacted with a dihaloalkane to yield a bridged diaryl halide. The bridged compound is then converted to a borane.

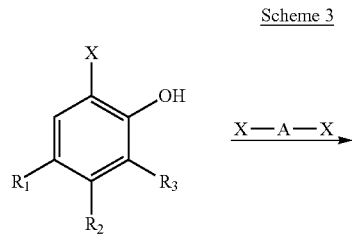

Scheme 3

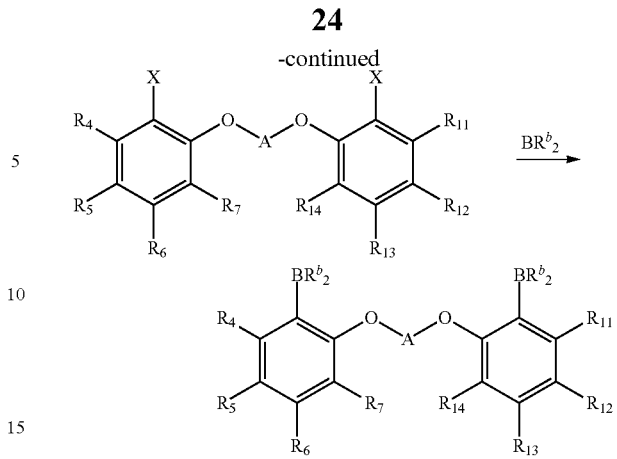

In Scheme 4, an arylated halophenol undergoes Suzuki coupling with a diaryl bridged borane to yield the target ligand.

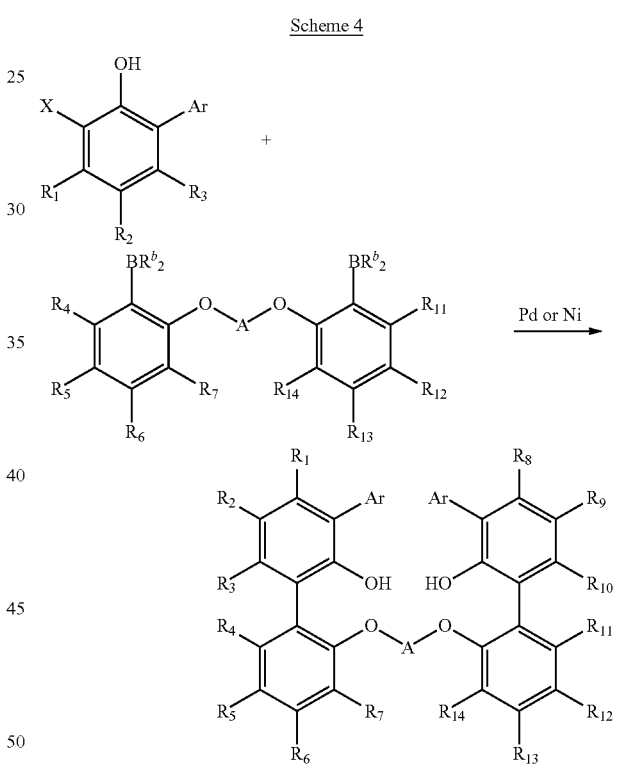

Scheme 4

A common feature of all of the reaction routes is that the phenol functionalities do not require protection.

In any one of the above methods each of $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ is independently selected from the group consisting of hydride, halide, optionally substituted hydrocarbyl, heteroatom-containing optionally substituted hydrocarbyl, alkoxy, aryloxy, silyl, boryl, dialkyl amino, alkylthio, arylthio and seleno; optionally two or more R groups can combine together into ring structures with such ring structures having from 3 to 100 non-hydrogen atoms in the ring; A is a bridging group having from one to 50 non-hydrogen atoms; Ar is optionally substituted aryl or heteroaryl.

In any one of the above methods each of $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ may be independently selected from the group consisting of hydride and optionally substituted aryl and hetroaryl.

In any of the above methods A may be selected from the group consisting of optionally substituted divalent alkyl, alkenyl, alkynyl, heteroalkyl, heteroalkenyl, heteroalkynyl, aryl, heteroaryl and silyl.

In any of the above methods the palladium catalyst may comprise a palladium phosphine compound, for example, bis(tri-tert-butylphosphine)palladium (Pd(PPh$_3$)$_4$), tetrakis (triphenylphosphine)palladium(0) (Pd(dppe)$_2$), bis[1,2-bis (diphenylphosphino)ethane]palladium(0) (Pd(dppf)), 1,1'-bis(diphenylphosphino)ferrocene palladium, and (2,2'-bis (diphenylphosphino)-1,1'-binaphthyl palladium (Pd (BINAP)).

In an illustrative embodiment and referring to the reaction scheme in FIG. 1: 2-Bromo-p-cresol, prepared from p-cresol, was combined with naphthalenylboronic acid and palladium tetrakistriphenylphosphine in THF. Sodium carbonate in water was added and the reaction heated to yield 4-methyl-2-naphthalenylphenol (1). (1) was treated with bromine to yield 2-bromo-4-methyl-6-naphthalenylphenol (2). 1,4-bis(2-bromophenoxy)butane was prepared from 2-bromophenol. Dibromoethane was added to magnesium turnings followed by bisbromophenoxybutane. Isopropylpinacolatoborolane was added to yield the pinacol borane 1,4-bis(2-(4,4,5,5-tetramethyl-1,3,2-dioxaborolan-2-yl)phenoxy)butane (3). Bispinacol borane (3) and bromonaphthalenylphenol (2) were dissolved in toluene. Potassium carbonate, palladium tetrakistriphenylphosphine and water were added to yield the ligand 2',2'''-(butane-1,4-diylbis (oxy))bis(5-methyl-3-naphthalenyl-[1,1'-biphenyl]-2-ol) (4).

Transition Metal Ligand Compounds

The transition metal ligand compounds may be prepared by any suitable synthesis method and the method of synthesis is not critical to the present disclosure. One useful method of preparing the transition metal ligand compounds of the present disclosure is by reacting a suitable metal compound, for example one having a displaceable anionic ligand, with the bridged bi-aromatic ligands of this disclosure. Non-limiting examples of suitable metal compounds include organometallics, metal halides, sulfonates, carboxylates, phosphates, organoborates (including fluoro-containing and other subclasses), acetonacetonates, sulfides, sulfates, tetrafluoroborates, nitrates, perchlorates, phenoxides, alkoxides, silicates, arsenates, borohydrides, naphthenates, cyclooctadienes, diene conjugated complexes, thiocyanates, cyanates, and the metal cyanides. The metal compound may be an organometallic or metal halide. The metal compound may be an organometallic.

The metal of the organometallic compound may be selected from Groups 1 to 16, or a transition metal selected from Groups 3 to 13 elements and Lanthanide series elements. The metal may be selected from Groups 3 to 7 elements. The metal may be a Group 4 metal, titanium, zirconium or hafnium.

The metal compound can, for example, be a metal hydrocarbyl such as: a metal alkyl, a metal aryl, a metal arylalkyl; a metal silylalkyl; a metal diene, a metal amide; or a metal phosphide. The metal compound may be a zirconium or hafnium hydrocarbyl.

An exemplary reaction is illustrated below.

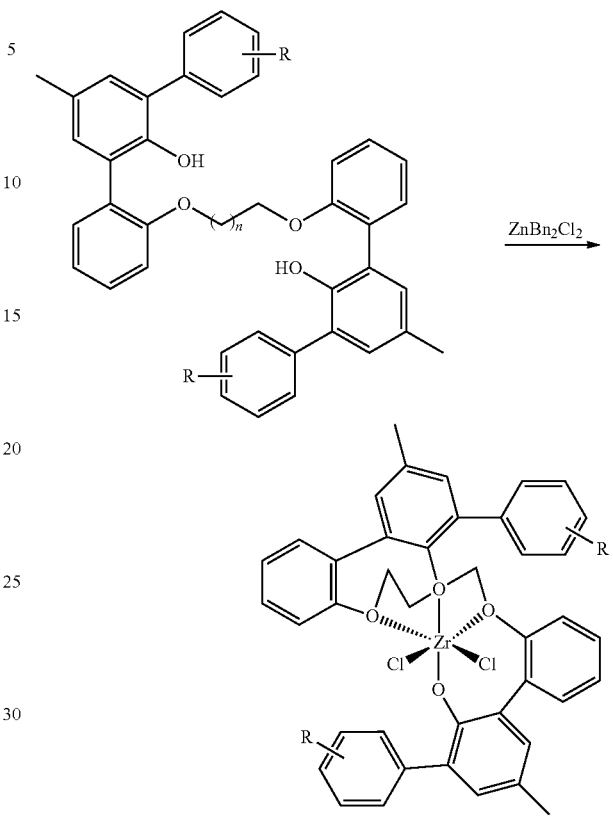

Examples of useful metal compounds include:
(i) tetramethylzirconium, tetraethylzirconium, zirconiumdichloride ($\eta^4$-1,4-diphenyl-1,3-butadiene), bis (triethylphosphine) and zirconiumdichloride ($\eta^4$-1,4-diphenyl-1,3-butadiene) bis (tri-n-propylphosphine), tetrakis [trimethylsilylmethyl]zirconium, tetrakis[dimethylamino] zirconium, dichlorodibenzylzirconium, chlorotribenzylzirconium, trichlorobenzylzirconium, bis[dimethylamino]bis[benzyl]zirconium, and tetrabenzylzirconium;
(ii) tetramethyltitanium, tetraethyltitanium, titaniumdichloride ($\eta^4$-1,4-diphenyl-1,3-butadiene), bis (triethylphosphine) and titaniumdichloride ($\eta^4$-1,4-diphenyl-1,3-butadiene) bis (tri-n-propylphosphine), tetrakis [trimethylsilylmethyl]titanium, tetrakis[dimethylamino] titanium, dichlorodibenzyltitanium, chlorotribenzyltitanium, trichlorobenzyltitanium, bis[dimethylamino]bis[benzyl]titanium, and tetrabenzyltitanium; and
(iii) tetramethylhafnium, tetraethylhafnium, hafniumdichloride ($\eta^4$-1,4-diphenyl-1,3-butadiene), bis (triethylphosphine) and hafniumdichloride ($\eta^4$-1,4-diphenyl-1,3-butadiene) bis (tri-n-propylphosphine), tetrakis [trimethylsilylmethyl]hafnium, tetrakis[dimethylamino] hafnium, dichlorodibenzylhafnium, chlorotribenzylhafnium, trichlorobenzylhafnium, bis[dimethylamino]bis[benzyl]hafnium, and tetrabenzylhafnium.

EXAMPLES

It is to be understood that while the present disclosure has been described in conjunction with the specific embodiments thereof, the foregoing description is intended to illustrate and not limit the scope of the disclosure. Other aspects, advantages and modifications will be apparent to those skilled in the art to which the disclosure pertains. Therefore, the following examples are put forth so as to provide those skilled in the art with a complete disclosure and description of how to make and use the disclosed compositions, and are not intended to limit the scope of the disclosure.

All reagents were purchased from commercial vendors and used as received unless otherwise noted. Solvents were sparged with $N_2$ and dried over 3 Å molecular sieves. Analytical thin-layer chromatography (TLC) was performed on Selecto Plates (200 μm) precoated with a fluorescent indicator. Visualization was effected using ultraviolet light (254 nm). Flash column chromatography was carried out with Sigma Aldrich Silica gel 60 Å (70-230 Mesh) using solvent systems specified. NMR spectra were recorded on a Bruker 400 or 500 NMR with chemical shifts referenced to residual solvent peaks.

Referring to FIG. 1: 4-methyl-2-naphthalenylphenol (1): 2-Bromo-p-cresol (1.4 g, 7.75 mmol), prepared from p-cresol, was combined with naphthalenylboronic acid (1.6 g, 9.3 mmol) and palladium tetrakistriphenylphosphine (80 mg, 0.07 mmol) and dissolved in 40 mL THF. Sodium carbonate (2.0 g, 19 mmol) dissolved in 60 mL of degassed water was added and the reaction heated at 80° C. for 3 days. The reaction was then cooled and extracted with ethyl acetate. The organic portion was washed with 10% HCl and brine, then dried (MgSO4), filtered and concentrated. Purification was achieved by silica gel chromatography (30% acetone/hexane), giving the product as a pale yellow oil in 77% yield: 1H NMR (500 MHz, CDCl3) δ 2.37 (s, 3H), 4.67 (s, 1H), 6.98 (d, J=9 Hz, 1H), 7.09 (s, 1H), 7.09 (m, 1H), 7.56 (m, 4H), 7.70 (d, J=8 Hz, 1H), 7.93 (m, 2H).

2-bromo-4-methyl-6-naphthalenylphenol (2): Compound (1) (1.4 g, 5.9 mmol) was dissolved in 5 mL dichloromethane. Bromine (0.45 mL, 8.85 mmol) was added slowly and the mixture stirred at ambient temperature overnight. It was then quenched with water and diluted with a portion of dichloromethane. The organic layer was washed with sodium metabisulfite and brine, then dried (MgSO4), filtered and concentrated. The brominated phenol (2) was obtained in 89% crude yield as a yellow oil and used without further purification: 1H NMR (400 MHz, CDCl3) δ 2.35 (s, 3H), 5.28 (d, J=4 Hz, 1H), 7.28 (d, J=8 Hz, 1H), 7.43 (m, 3H), 7.63 (m, 2H), 7.87 (d, J=8 Hz, 1H), 7.93 (d, J=8 Hz, 1H), 8.33 (m, 1H); IR (cm-1) 3508, 3045, 2920, 1469, 1234, 784.

1,4-bis(2-(4,4,5,5-tetramethyl-1,3,2-dioxaborolan-2-yl)phenoxy)butane (3): 1,4-bis(2-bromophenoxy) butane was prepared from 2-bromophenol. Dibromoethane (approx. 1 mL) was added to magnesium turnings (715 mg, 29.7 mmol) in 75 mL THF. After 10 minutes, bisbromophenoxybutane (5 g, 12.4 mmol) was added slowly and, once cool, the reaction was allowed to stir for 3 h. Isopropylpinacolatoborolane (5.04 mL, 24.8 mmol) was added and the reaction stirred for 15 min then poured onto ice. The mixture was extracted three times with ethyl acetate and the combined organic layers washed with brine, dried (MgSO4), filtered and concentrated giving the product as a pale yellow oil that turned solid upon standing. The pinacol borane (3) was used without further purification: 1H NMR (500 MHz, CDCl3) δ 1.35 (s, 24H), 2.10 (m, 4H), 4.06 (m, 4H), 6.86 (d, J=8 Hz, 2H), 6.94 (m, 3H), 7.37 (m, 2H), 7.65 (m, 2H); 13C NMR (100 MHz, CDCl3) 25.2 (8C), 26.1 (2C), 67.9 (2C), 83.6 (4C), 112.0 (2C), 120.5 (2C), 129.7 (2C), 132.6 (2C), 136.7 (2C), 164.0 (2C); IR (cm-1) 2977, 1599, 1444, 1354, 1244, 834.

2',2'''-(butane-1,4-diylbis(oxy))bis(5-methyl-3-naphthalenyl-[1,1'-biphenyl]-2-ol) (4): Bispinacol borane (3) and bromonaphthalenylphenol (2) were dissolved in toluene, giving a dark purple solution. Potassium carbonate (approx. 4.5 g), palladium tetrakistriphenylphosphine (100 mg, 0.86 mmol) and 10 mL of water were added and the reaction heated at 80° C. After heating overnight, the reaction was cooled and extracted three times with ethyl acetate. The combined organic layers were washed with 10% HCl and brine, then dried (MgSO4), filtered and concentrated. The orange/yellow oil was purified by silica gel column chromatography with 30% acetone/hexane eluent the give the product as a pale yellow solid: 1H NMR (500 MHz, CDCl3) δ 2.01 (m, 4H), 2.36 (s, 6H), 4.06 (m, 4H), 5.28 (s, 2H), 6.92 (m, 4H), 6.94 (m, 2H), 7.40 (m, 12H), 7.65 (m, 2H), 7.93 (m, 2H).

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited.

All documents cited are herein fully incorporated by reference for all jurisdictions in which such incorporation is permitted and to the extent such disclosure is consistent with the description of the present disclosure.

What is claimed is:

1. A method for preparing a bridged bi-aromatic phenol ligand of formula (I) from a compound containing at least one phenol group wherein the at least one phenol group remains unprotected during all steps of the method and the method comprises at least one step of aryl coupling;

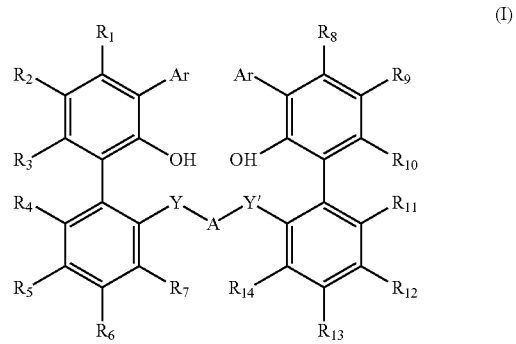

wherein each of $R^1$, $R^2$, $R^4$, $R^5$, $R^6$, $R^7$, $R^8$, $R^9$, $R^{10}$, $R^{11}$, $R^{12}$, $R^{13}$ and $R^{14}$ is independently selected from the group consisting of hydrogen, halide, optionally substituted hydrocarbyl, heteroatom-containing optionally substituted hydrocarbyl, alkoxy, aryloxy, silyl, boryl, dialkyl amino, alkylthio, arylthio and seleno; optionally two or more R groups combine together into ring structures with such ring structures having from 3 to 100 non-hydrogen atoms in the ring; A is a bridging group having from one to 50 non-hydrogen atoms; Y and Y' are independently selected from O, S, $NR^a$ and $PR^a$ wherein $R^a$ is optionally substituted hydrocarbyl; Ar is optionally substituted aryl or optionally substituted heteroaryl.

2. The method according to claim 1 comprising the step of:

treating an unprotected phenol of formula (II) with a compound of formula (III)

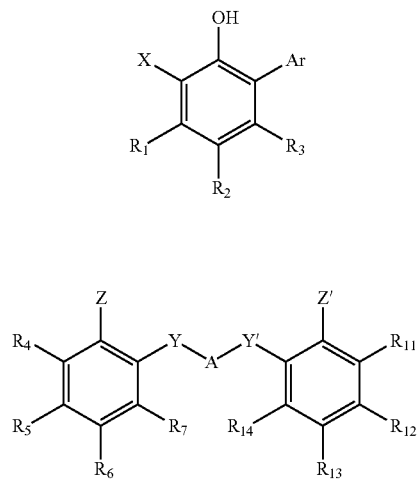

(II)

(III)

in the presence of a catalyst so as to form the compound of formula (I); wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ is independently selected from the group consisting of hydrogen, halide, optionally substituted hydrocarbyl, heteroatom-containing optionally substituted hydrocarbyl, alkoxy, aryloxy, silyl, boryl, dialkyl amino, alkylthio, arylthio and seleno; optionally two or more R groups combine together into ring structures with such ring structures having from 3 to 100 non-hydrogen atoms in the ring; A is a bridging group having from one to 50 non-hydrogen atoms; Y and Y' are independently selected from O, S, $NR^a$ and $PR^a$ wherein $R^a$ is optionally substituted hydrocarbyl; X is halide; Ar is optionally substituted aryl or optionally substituted heteroaryl; Z and Z' are independently selected from $BR^b_2$ and $BF_3^-$ $M^+$, wherein $R^b$ is independently selected from hydrogen, alkyl, hydroxy and alkoxy, wherein when both of $R^b$ are alkoxy, optionally they combine to form a ring structure of formula $BO_2R^b_2$, and wherein $M^+$ is an alkali metal cation.

3. The method according to claim 2 further comprising the steps of a) treating a compound of formula (IV) with a compound of formula (V);

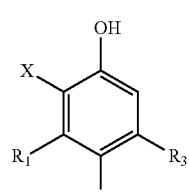

(IV)

$ArBR^b_2$ or (V)

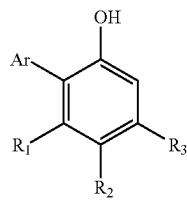

(VI)

in the presence of a catalyst so as to yield a compound of formula (VI); and b) treating the compound of formula (VI) with a source of halogen so as to yield the compound of formula (II);

wherein X is halide; $R^1$, $R^2$, $R^3$, Ar, $BR^b_2$ and $M^+$ are as defined in claim 2.

4. The method according to claim 2 further comprising the steps of:

a) halogenating a compound of formula (VII) to yield a compound of formula (VIII); and

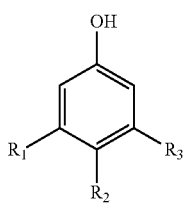

(VII)

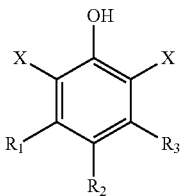

(VIII)

b) treating the compound of formula (VIII) with a compound of formula (V) in the presence of a catalyst to yield the compound of formula (II);

wherein X, $R^1$, $R^2$ and $R^3$ are as defined in claim 2.

5. The method according to claim 1 wherein the catalyst comprises a nickel or palladium catalyst.

6. The method according to claim 5 wherein the palladium catalyst comprises a palladium phosphine catalyst.

7. The method according to claim 5 wherein the palladium catalyst comprises bis(tri-tert-butylphosphine)palladium, tetrakis(triphenylphosphine)palladium(0) (Pd(PPh$_3$)$_4$), bis[1,2-bis(diphenylphosphino)ethane]palladium(0) (Pd(dppe)$_2$), 1,1'-bis(diphenylphosphino)ferrocene palladium (Pd(dppf)), or (2,2'-bis(diphenylphosphino)-1,1'-binaphthyl palladium (Pd(BINAP).

8. The method according to claim 2 wherein the catalyst further comprises a base.

9. The method according to claim 8 wherein the base comprises an alkali metal carbonate, alkali metal phosphate, alkali metal hydroxide, alkali metal alkoxide or an amine.

10. The method according to claim 2 wherein X is bromo or chloro.

11. The method according to claim 1 comprising the steps of:

a) treating a compound of formula (IV) with a compound of formula (V) in the presence of a catalyst so as to yield a compound of formula (VI);

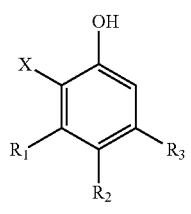

(IV)

ArBR$^b_2$ or ArBF$_3^-$M$^+$ (V)

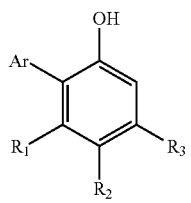

(VI)

b) treating the compound of formula (VI) with a source of halogen so as to yield the compound of formula (II); and c) treating the unprotected phenol of formula (II) with a compound of formula (III) to yield the compound of formula (I);

wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ is independently selected from the group consisting of hydrogen, halide, optionally substituted hydrocarbyl, heteroatom-containing optionally substituted hydrocarbyl, alkoxy, aryloxy, silyl, boryl, dialkyl amino, alkylthio, arylthio and seleno; optionally two or more R groups combine together into ring structures with such ring structures having from 3 to 100 non-hydrogen atoms in the ring; A is a bridging group having from one to 50 non-hydrogen atoms; Y and Y' are independently selected from O, S, NR$^a$ and PR$^a$ wherein R$^a$ is optionally substituted hydrocarbyl; X is halide; Ar is optionally substituted aryl or optionally substituted heteroaryl; Z and Z' are independently selected from BR$^b_2$ and BF$_3^-$M$^+$, wherein R$^b$ is independently selected from hydrogen, alkyl, hydroxy and alkoxy, wherein when both of R$^b$ are alkoxy, optionally they combine to form a ring structure of formula BO$_2$R$^b_2$, and wherein M$^+$ is an alkali metal cation.

12. The method according to claim 1 wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ is independently selected from the group consisting of hydrogen, halide, optionally substituted alkyl, heteroalkyl, aryl, heteroaryl, alkoxyl, aryloxyl, silyl, boryl, dialkylamino, alkylthio, arylthio, and seleno.

13. The method according to claim 1 wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ is independently selected from the group consisting of hydrogen, halide, optionally substituted alkyl, heteroalkyl, aryl, heteroaryl, alkoxyl, aryloxyl, silyl, dialkylamino, alkylthio, and arylthio.

14. The method according to claim 1 wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ is independently selected from the group consisting of hydrogen, and optionally substituted alkyl and aryl.

15. The method according to claim 1 wherein the bridging group A is selected from the group consisting of optionally substituted divalent hydrocarbyl and divalent heteroatom containing hydrocarbyl.

16. The method according to claim 1 wherein the bridging group A is selected from the group consisting of optionally substituted divalent alkyl, alkenyl, alkynyl, heteroalkyl, heteroalkenyl, heteroalkynyl, carbocycle, heterocarbocycle, aryl, heteroaryl and silyl.

17. The method according to claim 1 wherein the bridging group A is an optionally substituted divalent alkyl.

18. A method according to claim 1 wherein the bridging group A is represented by the general formula -(QR$^{15}_{2-z''}$)$_{z'}$— wherein each Q is either carbon or silicon and each R$^{15}$ is the same or different from the others such that each R$^{15}$ is selected from the group consisting of hydrogen and optionally substituted hydrocarbyl and heteroatom containing hydrocarbyl, and optionally two or more R$^{15}$ groups join into a ring structure having from 3 to 50 atoms in the ring structure not counting hydrogen atoms; z' is an integer from 1 to 10; and z'' is 0, 1 or 2.

19. The method according to claim 1 wherein Ar is selected from optionally substituted phenyl, naphthyl, biphenyl, anthracenyl, and phenanthrenyl.

20. The method according to claim 1 wherein Ar is selected from thiophene, pyridine, isoxazole, pyrazole, pyrrole, furan or benzo-fused analogues of these rings.

* * * * *